United States Patent [19]

McKerns

[11] 4,193,915

[45] Mar. 18, 1980

[54] CONTRACEPTIVE, ANTIBODY GENERATING, POLYPEPTIDES

[76] Inventor: Kenneth W. McKerns, Blue Hill Falls, Me. 04615

[21] Appl. No.: 896,225

[22] Filed: Apr. 13, 1978

[51] Int. Cl.[2] .................... C07C 103/52; A61K 37/00
[52] U.S. Cl. ............................. 260/112.5 R; 424/177
[58] Field of Search .................. 260/112.5 R; 424/177

[56] References Cited

U.S. PATENT DOCUMENTS

| | | | |
|---|---|---|---|
| 4,031,069 | 6/1977 | Nicolaides et al. | 260/112.5 R |
| 4,031,071 | 6/1977 | Wittle et al. | 260/112.5 R |
| 4,043,994 | 8/1977 | Wittle et al. | 260/112.5 R |
| 4,086,219 | 4/1978 | Wittle et al. | 260/112.5 R |

FOREIGN PATENT DOCUMENTS 558316  12/1943  United Kingdom ............. 260/112.5 R

*Primary Examiner*—Delbert R. Phillips
*Attorney, Agent, or Firm*—Finnegan, Henderson, Farabow & Garrett

[57] ABSTRACT

Polypeptides D-Ser-Arg-Tyr-Gly-Pro-Val-Gly-Val-NH$_2$, D-Ser-Arg-Ala-Tyr-Pro-Thr-Pro-Ala-Arg-Ser-Lys-Lys-NH$_2$, D-Ser-Arg-Tyr-Gly-Lys-Pro-Val-Gly-Lys-Lys-Lys-Lys-NH$_2$, D-Ser-Arg-Tyr-Gly-Lys-Pro-Val-Arg-Ser-Lys-Lys-NH$_2$, D-Ser-Arg-Tyr-Gly-Pro-Val-NH$_2$, D-Ser-Arg-Tyr-Gly-Lys-Pro-Val-Gly-Lys-Lys-Val-NH$_2$, D-Ser-Arg-Leu-Pro-Gly-Pro-Ser-NH$_2$, D-Ser-Arg-Val-Leu-Val-Gly-Val-NH$_2$, D-Ser-Arg-Val-Leu-Pro-Val-NH$_2$, D-Ser-Arg-Ala-Tyr-Pro-Thr, D-Ser-Arg-Val-Leu-Gln-Gly-Val-NH$_2$, D-Ser-Arg-Ala-Tyr-Pro-Arg-Leu-Pro-Gly-Pro-NH$_2$, D-Ser-Arg-Ala-Tyr-Pro-Arg-Val-Leu-Gln-Gly-Val-NH$_2$, D-Ser-Arg-Ala-Tyr-Pro-Arg-Val-Leu-Pro-Val-NH$_2$, are useful as contraceptives.

28 Claims, No Drawings

CONTRACEPTIVE, ANTIBODY GENERATING, POLYPEPTIDES

BACKGROUND OF THE INVENTION

Both the theoretical spectre of overpopulation and modern economic exigencies have occasioned concern for limiting the human reproductive process. In recent years, great interest has focused on chemical methods for limiting reproduction, including the use of steroids, anti-steroids, polypeptides, antibodies and proteins, and compounds blocking the release or synthesis of the luteinizing hormone, synonymously referred to as lutropin (LH).

Specifically, various polypeptides are known to have contraceptive properties. For example, U.S. Pat. No. 4,016,259 to Kent, Jr. teaches a tetrapeptide, useful as a contraceptive with the following basic amino acid sequence subject to modifications: Thr-Pro-Arg-Lys. Furthermore, U.S. Pat. Nos. 3,855,199 to Foell et al, 3,886,135 to McKinley et al, 3,886,137 to Yardley, 3,928,307 to Foell et al, 3,937,695 to Sarantakis, 3,940,380 to Garsky and 3,941,763 to Sarantakis all teach polypeptides, either exhibiting anti-ovulating activity in mammals or inhibiting LH (lutropin) release, with the basic amino acid sequence p-Glu-D-Phe-Trp-Ser-Tyr-D-Ala-Leu-Arg-Pro-Gly-NH$_2$, with substitutions or deletions in the amino acid sequences. Finally, U.S. Pat. No. 3,915,947 to Shields teaches a contraceptive compound L Pyroglu-L-Trp-L-Ser-L-Tyr-D-Ala-L-Leu-L-Arg-L-Pro-NHCH$_2$CH$_3$.

A vigorous search continues for more effective compounds having minimal side effects which can be produced in large quantities at reasonable cost.

SUMMARY OF THE INVENTION

The invention comprises a series of polypeptides synthesized by solid phase peptide procedures. These polypeptides, structurally different from all known prior art polypeptide contraceptives, block the action of human choriogonadotropin (hCG) and LH in the first few days of mammalian pregnancy by successfully competing with these natural hormones within the receptor cells in the ovary. Further, the compounds have the potential to block hCG action at any time in the first trimester of human pregnancy and also inhibit LH action on the testes. Accordingly, the inventive compounds, which compete with the natural hormones, differ in mechanism from those in the prior art which block the release or synthesis of LH.

Because the synthetic peptides successfully compete with the natural hormones LH and hCG in the receptor cells in the ovaries and testes to block their stimulating action, they are useful for contraceptive purposes. If, for example, administered to a non-pregnant female during the estrus or menstrual cycle, the compound terminates the cycle by blocking the action of LH. Alternatively, if the compounds are given in early pregnancy, or at the end of the menstrual cycle, they block the action of the gonadotropin hCG coming from the chorion cells of the fertilized ovum, either preventing implantation or terminating pregnancy if the ovum has implanted itself in the uterus.

In accordance with the invention, the following compounds are provided which are capable of solid phase peptide synthesis, and which have the qualities and uses specified above: a compound R$_1$-R$_2$-R$_3$ and its pharmacologically acceptable salts, wherein R$_1$ is chosen from the group consisting of D-Ser-Arg, Ser-Arg, and -Arg, R$_2$ is chosen from the group consisting of Tyr-Gly-Lys-Pro-Val-Gly-Lys-Lys, Ala-Tyr-Pro-Thr-Pro-Ala-Arg-Ser-Lys, Tyr-Gly-Lys-Pro-Val-Gly-Lys-Lys-Lys, Tyr-Gly-Lys-Pro-Val-Arg-Ser-Lys, Tyr-Gly-Pro, Tyr-Gly-Pro-Val-Gly, Val-Leu-Pro, Val-Leu-Val-Gly, Ala-Tyr-Pro, Leu-Pro-Gly-Pro, Val-Leu-Gln-Gly, Ala-Tyr-Pro-Arg-Leu-Pro-Gly, Ala-Tyr-Pro-Arg-Val-Leu-Gln-Gly and Ala-Tyr-Pro-Arg-Val-Leu-Pro, and R$_3$ is chosen from the group consisting of Val-NH$_2$, -Val, Lys-NH$_2$, -Lys, -Thr, Thr-NH$_2$, -Ser, Ser-NH$_2$, -Pro and -Pro-NH$_2$.

Included within this broad statement of the invention are the following compounds, capable of solid phase peptide synthesis, which have the qualities and uses specified above: a compound comprising R$_1$-Tyr-Gly-Lys-Pro-Val-Gly-Lys-Lys-R$_4$, and its pharmacologically acceptable salts wherein R$_1$ is as described above and R$_4$ is chosen from the group consisting of -Val-NH$_2$ and -Val; a compound comprising R$_1$-Ala-Tyr-Pro-Thr-Pro-Ala-Arg-Ser-Lys-R$_5$, and its pharmacologically acceptable salts wherein R$_1$ is as described above and R$_5$ is chosen from the group consisting of -Lys-NH$_2$ and -Lys; a compound comprising R$_1$-Tyr-Gly-Lys-Pro-Val-Gly-Lys-Lys-Lys-R$_5$ and its pharmacologically acceptable salts wherein R$_1$ and R$_5$ are as described above; a compound comprising R$_1$-Tyr-Gly-Lys-Pro-Val-Arg-Ser-Lys-R$_5$, and its pharmacologically acceptable salts wherein R$_1$ and R$_5$ are as described above; a compound comprising R$_1$-Tyr-Gly-R$_6$ and its pharmacologically acceptable salts, wherein R$_1$ is as described above and R$_6$ is chosen from the group consisting of Pro-R$_4$ and Pro-Val-Gly-R$_4$, wherein R$_4$ is as described above; a compound comprising R$_1$-Val-Leu-Val-Gly-R$_4$ and its pharmacologically acceptable salts, wherein R$_1$ and R$_4$ are as described above; a compound comprising R$_1$-Leu-Pro-Gly-Pro-R$_7$ and its pharmacologically acceptable salts, wherein R$_1$ is as described above and R$_7$ is chosen from the group consisting of Ser-NH$_2$ and -Ser; a compound comprising R$_1$-Val-Leu-Gln-Gly-R$_4$ and its pharmacologically acceptable salts, wherein R$_1$ and R$_4$ are as described above; a compound comprising R$_1$-Ala-Tyr-Pro-Arg-Leu-Pro-Gly-R$_8$, and its pharmacologically acceptable salts, wherein R$_1$ is as described above and R$_8$ is chosen from the group consisting of Pro-NH$_2$ and -Pro; a compound comprising R$_1$-Ala-Tyr-Pro-Arg-Val-Leu-Gln-Gly-R$_4$, and its pharmacologically acceptable salts wherein R$_1$ and R$_4$ are as described above; a compound comprising R$_1$-Ala-Tyr-Pro-Arg-Val-Leu-Pro-R$_4$ and its pharmacologically acceptable salts wherein R$_1$ and R$_4$ are as described above; and a compound R$_1$-Ala-Tyr-Pro-R$_9$, and its pharmacologically acceptable salts, wherein R$_1$ is as described above and R$_9$ is chosen from the group consisting of -Thr and Thr-NH$_2$.

Specifically, the following compounds have been synthesized: D-Ser-Arg-Tyr-Gly-Lys-Pro-Val-Gly-Lys-Lys-Val-NH$_2$; D-Ser-Arg-Ala-Tyr-Pro-Thr-Pro-Ala-Arg-Ser-Lys-Lys-NH$_2$; D-Ser-Arg-Tyr-Gly-Lys-Pro-Val-Gly-Lys-Lys-Lys-NH$_2$; D-Ser-Arg-Tyr-Gly-Lys-Pro-Val-Arg-Ser-Lys-Lys-NH$_2$; D-Ser-Arg-Tyr-Gly-Pro-Val-NH$_2$; D-Ser-Arg-Tyr-Gly-Pro-Val-Gly-Val-NH$_2$; and D-Ser-Arg-Val-Leu-Pro-Val-NH$_2$.

An advantage of the peptides of this invention is that they can be utilized in the form of pharmacologically acceptable salts. These salts have the advantage of increased water solubility and are particularly useful for parenteral administration. Examples of such salts are sodium, potassium, calcium, acetates, and chlorides. Such examples are representative rather than exclusive.

Because of the unknown folding of the three-dimensional structures of globular models of LH and hCG, the active center of these hormones is unknown. Further, their mechanism of action is a matter of dispute. It is believed that the structural sequence of the inventive compounds is similar to a significant part of the active center of the hormones LH and hCG. This is especially so in regard to Ser-Arg-Leu-Pro-Gly-Pro-Ser which corresponds to AA residues 132-138 in the beta subunit of hCG, and Arg-Val-Leu-Gln-Gly-Val-NH$_2$ which corresponds to AA 43-48 in the beta subunit of hCG, and Arg-Val-Leu-Pro-Val which corresponds to AA 43-47 in the beta subunit of LH. The sequence Ser-Arg-Ala-Tyr-Pro-Thr corresponds to AA 38-43 in the alpha subunit of LH. The sequence Ser-Arg-Ala-Tyr-Pro corresponds to AA 34-38 in the alpha subunit of hCG. It seems likely that these sequences in the alpha and beta subunits of LH and hCG are involved in the active center of the hormones.

Accordingly, it is believed that the following compounds also have the qualities and contraceptive uses described above and are thus within the scope of the invention: D-Ser-Arg-Val-Leu-Gln-Gly-Val-NH$_2$ and its pharmacologically acceptable salts; D-Ser-Arg-Ala-Tyr-Pro-Arg-Leu-Pro-Gly-Pro-NH$_2$ and its pharmacologically acceptable salts, D-Ser-Arg-Ala-Tyr-Pro-Arg-Val-Leu-Gln-Gly-Val-NH$_2$ and its pharmacologically acceptable salts; D-Ser-Arg-Ala-Tyr-Pro-Arg-Val-Leu-Pro-Val-NH$_2$ and its pharmacologically acceptable salts; D-Ser-Arg-Leu-Pro-Gly-Pro-Ser-NH$_2$ and its pharmacologically acceptable salts; D-Ser-Arg-Val-Leu-Pro-Val-NH$_2$ and its pharmacologically acceptable salts; and D-Ser-Arg-Ala-Tyr-Pro-Thr-NH$_2$ and its pharmacologically acceptable salts.

For convenience, the standard abbreviations for amino acids are used:
- Ala—Alanine
- Arg—Arginine
- Gly—Glycine
- Gln—Glutamine
- Leu—Leucine
- Lys—Lysine
- Pro—Proline
- Ser—Serine
- Thr—Threonine
- Tyr—Tyrosine
- Val—Valine All amino acids in the formulas herein described are in the natural configuration, except, in some instances, Ser, which is denoted in such cases as D-Ser.

In the synthesized peptides, the amino terminal acid is preferably a D-Ser isomer rather than the natural Ser configuration, and the carboxyl end is preferably an amide. Both of these structural variations decrease the rate of degradation by proteolytic enzymes, although neither is an essential feature of the structure.

The most effective relevant compound for contraceptive purposes, so far discovered, is D-Ser-Arg-Tyr-Gly-Pro-Val-Gly-Val-NH$_2$, hereinafter referred to as E$_2$. The specificity of this sequence of amino acids is shown by the fact that the peptide, D-Ser-Pro-Val-Gly-Val-NH$_2$, without the Arg-Tyr-Gly amino acid sequence, is relatively ineffective in inhibiting the action of hCG or LH. It is believed that synthesized compound D-Ser-Arg-Tyr-Gly-Pro-Val-NH$_2$ is an inhibitor of hCG and LH because it contains the Arg-Tyr-Gly amino acid sequence.

A great number of other modifications and amino acid substitutions are within the scope of the invention. Because the sites of action of all of the proteolytic enzymes are well known, the skilled artisan can substitute other amino acids, D-isomers, or modifications of the amino acids to resist enzymatic cleavage and lengthen the effective life of the compounds. Specifically it is believed that D-Ser-Arg-Val-Leu-Val-Gly-Val-NH$_2$ is within the scope of the invention.

Further, in a compound R$_1$-Tyr-Gly-R$_6$, described above, Tyr may be substituted by an amino acid chosen from the group consisting of Ala, Val, and Leu, Gly may be substituted by an amino acid chosen from the group consisting of Tyr, Leu, and Pro, and Val-NH$_2$ may be substituted by a compound chosen from the group consisting of Pro-NH$_2$, Gly, -Thr and Thr-NH$_2$. Specifically, a compound may comprise D-Ser-Arg-Ala-Tyr-Pro-Thr and its pharmacologically acceptable salts. A compound may also comprise D-Ser-Arg-Val-Leu-Pro-Val-NH$_2$ and its pharmacologically acceptable salts.

The invention further comprises a method of preventing or terminating pregnancy in mammals comprising the step of introducing into the system of a mammal an effective amount of a compound R$_1$-R$_2$-R$_3$ and its pharmacologically acceptable salts, wherein R$_1$ is chosen from the group consisting of D-Ser-Arg Ser-Arg, and -Arg, R$_2$ is chosen from the group consisting of Tyr-Gly-Lys-Pro-Val-Gly-Lys-Lys, Ala-Tyr-Pro-Thr-Pro-Ala-Arg-Ser-Lys, Tyr-Gly-Lys-Pro-Val-Gly-Lys-Lys-Lys, Tyr-Gly-Lys-Pro-Val-Arg-Ser-Lys, Tyr-Gly-Pro, Tyr-Gly-Pro-Val-Gly, Val-Leu-Pro, Val-Leu-Val-Gly, Ala-Tyr-Pro, Leu-Pro-Gly-Pro, Val-Leu-Gln-Gly, Ala-Tyr-Pro-Arg-Leu-Pro-Gly, Ala-Tyr-Pro-Arg-Val-Leu-Gln-Gly and Ala-Tyr-Pro-Arg-Val-Leu-Pro, and R$_3$ is chosen from the group consisting of Val-NH$_2$, -Val, Lys-NH$_2$, -Lys, -Thr, Thr-NH$_2$, -Ser, Ser-NH$_2$, -Pro and -Pro-NH$_2$.

The invention also comprises a method of causing temporary sterility in mammals comprising the step of introducing into the system of the patient an effective amount of a compound R$_1$-R$_2$-R$_3$ and its pharmacologically acceptable salts, wherein R$_1$ is chosen from the group consisting of D-Ser-Arg, Ser-Arg, and -Arg, R$_2$ is chosen from the group consisting of Tyr-Gly-Lys-Pro-Val-Gly-Lys-Lys, Ala-Tyr-Pro-Thr-Pro-Ala-Arg-Ser-Lys, Tyr-Gly-Lys-Pro-Val-Gly-Lys-Lys-Lys, Tyr-Gly-Lys-Pro-Val-Arg-Ser-Lys, Tyr-Gly-Pro, Tyr-Gly-Pro-Val-Gly, Val-Leu-Pro, Val-Leu-Val-Gly, Ala-Tyr-Pro, Leu-Pro-Gly-Pro, Val-Leu-Gln-Gly, Ala-Tyr-Pro-Arg-Leu-Pro-Gly, Ala-Tyr-Pro-Arg-Val-Leu-Gln-Gly and Ala-Tyr-Pro-Arg-Val-Leu-Pro, and R$_3$ is chosen from the group consisting of Val-NH$_2$, -Val, Lys-NH$_2$, -Lys, -Thr, Thr-NH$_2$, -Ser, Ser-NH$_2$, -Pro and -Pro-NH$_2$.

The inventive compounds are believed to be useful for preventing or terminating pregnancy in mammals by generating antibodies against LH or hCG in order to inhibit either LH-induced ovulation or the maintenance of pregnancy by hCG. The potential exists for generating antibodies in humans specific for the hCG of early pregnancy without reacting with LH or interfering with the normal menstrual cycle. Thus, women could be vaccinated against pregnancy by administering the inventive compounds in a suitable adjuvant once every six months or year to maintain the antibody level. Accordingly, the invention is also directed to a method of preventing or terminating pregnancy by generating antibodies in mammals against LH or hCG comprising the steps of linking to a suitable adjuvant a compound $R_1$-$R_2$-$R_3$ and its pharmacologically acceptable salts, wherein $R_1$ is chosen from the group consisting of D-Ser-Arg, Ser-Arg and Arg, $R_2$ is chosen from the group consisting of Tyr-Gly-Lys-Pro-Val-Gly-Lys-Lys, Ala-Tyr-Pro-Thr-Pro-Ala-Arg-Ser-Lys, Tyr-Gly-Lys-Pro-Val-Gly-Lys-Lys-Lys, Tyr-Gly-Lys-Pro-Val-Arg-Ser-Lys, Tyr-Gly-Pro, Tyr-Gly-Pro-Val-Gly, Val-Leu-Pro, Val-Leu-Val-Gly, Ala-Tyr-Pro, Leu-Pro-Gly-Pro, Val-Leu-Gln-Gly, Ala-Tyr-Pro-Arg-Leu-Pro-Gly, Ala-Tyr-Pro-Arg-Val-Leu-Gln-Gly and Ala-Tyr-Pro-Arg-Val-Leu-Pro, and $R_3$ is chosen from the group consisting of Val-$NH_2$, -Val, Lys-$NH_2$, -Lys, -Thr, Thr-$NH_2$, -Ser, Ser-$NH_2$, -Pro and -Pro-$NH_2$.

The method of such linking has been well demonstrated by workers in the prior art who have raised antibodies in Rhesus monkeys against hCG and tetanus toxoid by injecting a beta-subunit of hCG coupled to tetanus toxoid, using gluteraldehyde as the coupling reagent. See 13 Contraception 153 (1976).

The compound $E_2$ also inhibits ovarian glucose-6-phosphate dehydrogenase, and thus inhibits synthetic pathways concerned with RNA, and protein and steroid biosyntheses.

DETAILED DESCRIPTION OF THE PREFERRED EMBODIMENTS

Great numbers of procedures are available for the synthesis of polypeptides from amino acids. The chemistry and methodology for the solid phase procedure for the synthesis of polypeptides from amino acids is described in various prior art references such as Stuart & Young, *Solid Phase Peptide Synthesis* (1968). The equipment, amino acids, and other chemicals necessary to perform the syntheses are readily obtainable commercially.

In this detailed description of the invention, the following standard abbreviations are essentially those recommended by the IUPAC-IUB Commission on Biochemical Nomenclature as published in 241 J. Biol. Chem. 241 (1966) and 242 J. Biol. Chem. 55 (1967):

| | |
|---|---|
| Aoc | t-amyloxycarboxyl |
| Boc | t-butyloxycarboxyl |
| Bzl | benzyl |
| $CH_2Cl_2$ | methylene chloride |
| Cl-Z | chlorocarbobenzoxy |
| DCC | dicyclohexylcarbodiimide |
| DCHA | dicyclohexylamine |
| DMF | dimethylformamide |
| MeOH | methanol |
| TBA | t-butylamine |
| TEA | triethylamine |
| TFA | trifluoroacetic (anhydrous) |
| Tos | p-toluenesulfonyl |
| Z | carbobenzoxy |

Further, amino acid will be abbreviated AA.

Example I demonstrates in detail the synthesis of the inventive compounds. Example I and the other Examples are not to be construed as a limitation of the invention. Various other modifications and equivalents of the examples would suggest themselves to those skilled in the art without departing from the spirit or scope of the present invention. In addition to the abbreviations already detailed, various standard abbreviations well recognized by those skilled in the art are employed.

Because a C-terminal amide was desired to resist enzymatic cleavage, benzhydrylamine (BHA) resin, purchased from Beckman Bioproducts Department, Palo Alto, Calif. 94304, was used for the solid-phase peptide synthesis. Alternatively, if a free carboxyl terminal is required, a resin such as the readily available Merrifield resin can be used.

EXAMPLE I—Synthesis of D-Ser-Arg-Tyr-Gly-Lys-Pro-Val-Gly-Lys-Lys-Val-$NH_2$

A. Coupling of first Boc--AA to BHA resin

Three grams of BHA resin were put into a 50 ml polypropylene reaction vessel having a filter disk. After adding 75 ml of 25%-by-vol solution of triethylamine (TEA) in $CH_2Cl_2$, the resin was stirred for 10 minutes to liberate the free amine. The TEA solution was then drawn off and the resin washed four times with 20 ml $CH_2Cl_2$ amounts. 571 mg or 2.5 milliequivalents (meq) per gram resin of Boc-Val in a 5 ml $CH_2Cl_2$ solution were added and mixed briefly. The coupling agent DCC in $CH_2Cl_2$ was added in an amount equimolar to the Boc-Val, 2.5 m mol/g resin, and mixed for 2 hours. After mixing, the solution was drawn off and the resin was washed three times with 20 ml $CH_2Cl_2$ solutions. To eliminate residual amino groups on the resin, 75 ml of 25% TEA in $CH_2Cl_2$ was added and mixed for 10 minutes. Subsequently, the TEA solution was drawn off and 10 mole/amine mole of acetic anhydride in $CH_2Cl_2$ was added and mixed for 10 minutes. This was followed by three washings with 20 ml solutions of $CH_2Cl_2$. These washings were followed by three washings with 20 ml solutions of MeOH. After the washings, the solutions were drawn off and the resin dried in vacuo. An aliquot of resin was subsequently hydrolysed with HCl. The AA analysis showed 0.35 meq of Val coupled to the amine.

B. Coupling of second amino acid, Lys, obtained as Boc-Lys (Cl-Z).TBA.

The Boc-Lys (Cl-Z) acid was prepared from the commercially obtained TBA salt before coupling by suspending two grams of the powdered TBA salt in 10 ml ethyl acetate and then adding 12 meq, 12 ml, of 1 N aqueous sulfuric acid. The solution was then shaken until the salt completely dissolved. The two resulting layers were separated and the aqueous layer re-extracted twice with fresh ethyl acetate. The ethyl acetate extracts were combined and washed twice with water and once with saturated sodium chloride solution. The washed extracts were dried over anhydrous sodium sulfate. Concentration of the dry solution yielded an oily material, the free Boc-Lys acid, which was subsequently dissolved in $CH_2Cl_2$.

Deprotection and amino acid coupling of 3 g of the resin-Val and the Boc-Lys acid were carried out by the following steps: (1) Three washings with 20 ml solutions of $CH_2Cl_2$; (2) a prewashing for 2 minutes with 20 ml of 25% TFA in $CH_2Cl_2$; (3) a washing with 20 ml TFA/$CH_2Cl_2$ for 30 minutes; (4) five washings with 20 ml solutions of $CH_2Cl_2$; (5) a two minute prewashing with 20 mls of 10% TEA in $CH_2Cl_2$; (6) a washing for 10 minutes with 20 ml of TEA/$CH_2Cl_2$; (7) five washings with 20 ml solutions of $CH_2Cl_2$; (8) addition of 931 mg of the prepared Boc-Lys (Cl-Z) solution in approximately 5 ml CH$_2$Cl$_2$; (9) addition and mixing of approximately 2.5 meq, 1.25 ml, of 2 M DCC in CH$_2$Cl$_2$; (10) mixing for 90 minutes; (11) three washings with 20 ml solutions of CH$_2$Cl$_2$; (12) three washings with 20 ml solutions of MeOH; (13) three washings with 20 ml solutions of CH$_2$Cl$_2$; (14) a two minute prewashing with 20 ml of 10% TEA/CH$_2$Cl$_2$; (15) a washing for 10 minutes with 20 ml TEA/CH$_2$Cl$_2$; (16) five washings with 20 ml solutions of CH$_2$Cl$_2$; (17) addition and mixing of 931 mg of the prepared Boc-Lys (Cl-Z) solution in CH$_2$Cl$_2$; (18) addition of 2.5 meq DCC in CH$_2$Cl$_2$; (19) mixing for 90 minutes; (20) three washings with 20 ml solutions of CH$_2$Cl$_2$; (21) three washings with 20 ml solutions of MeOH; and (22) three washings with 20 ml solutions of CH$_2$Cl$_2$.

The above 22 steps were repeated for each of the amino acids of the compound D-Ser-Arg-Tyr-Gly-Lys-Pro-Val-Gly-Lys-Lys-Val-NH$_2$, coupling the following sequence of Boc-or Aoc-amino acids of the amounts indicated: 931 mg Boc-Lys (Z); 460 mg Boc-Gly; 570 mg Boc-Val; 538 mg Boc-Pro; 931 mg Boc-Lys (Cl-Z); 460 mg Boc-Gly; 929 mg Boc-Tyr(Bzl); 883 mg Aoc-Arg; 738 mg Boc-D-Ser (Bzl).

If the Boc-D-Ser(Bzl) is obtained as a DCHA salt, the Boc-D-Ser(Bzl) acid must be separated from the DCHA salt before coupling. This is accomplished by the procedure, described above, used to separate Boc-Lys(Cl-Z) acid from the TBA salt.

The final peptide resin was washed after step 22 with MeOH, dried, and stored in a glass desiccator in the refrigerator. The weight was 3.710 g. The protecting groups were removed and an aliquot, 1.85 g, of the above 11 amino acid peptide-resin was cleaved by treatment with approximately 15 ml liquid hydrogen fluoride containing 5 ml anisole for 1 hour at 0° C. The hydrogen fluoride was removed by vacuum distillation and the anisole removed by ethyl acetate using filtration means.

To remove the peptide from the resin by filtration, the resin was washed several times with small volumes of 50% acetic acid. The combined filtrates were then lyophilized to obtain the desired peptide.

For purification purposes, the peptide was dissolved in a minimum volume of 0.5 M acetic acid and applied to a gel filtration column of Sephadex G-25F, 1.6 cm $\times$ 190 cm long, equilibrated with 0.5 M acetic acid. The peptide was eluted with the same solvent and monitored by UV analysis. The fractions corresponding to the major peak were pooled and lyophilized to obtain 200 mg white fluffy powder.

For further purification by column partition chromatography, see Yomashiro, 201 Nature 76 (1964), a partition column of Sephadex G-25F, 1.5 cm $\times$ 190 cm long, was prepared by equilibration with lower phase and then upper phase of the BAW solvent system (n-butanol:acetic acid:water, 4:1:5, $V_H$ = 120 ml). The lyophilized peptide obtained by gel filtration was applied in 1.5 ml of upper phase. Elution with upper phase yielded one major peptide zone located as described above. After pooling and lyophilization, 90 mg of a white fluffy powder was obtained.

Amino acid analysis by a Beckman/Spinco analyzer of hydrolyzates of this material yielded ratios close to the expected values for the following amino acids: Ser(1), Arg(1), Tyr(1), Lys(3), Pro(1), Val(2), Gly(2), NH$_3$(1). 20 $\mu$g loads of the peptide were homogeneous in acidic, neutral and basic thin layer chromatography systems when examined under ultraviolet light, iodine vapor, and Pauly reagent by methods described in Monahan et al, 47 Biochem. Biophys. Res. Commun. 551 (1972).

The synthesis illustrated in this example can be applied to all of the inventive polypeptides, using the appropriate Boc- or Aoc-amino acids in the correct sequence. For example, to make the compound D-Ser-Arg-Ala-Tyr-Pro-Thr-Pro-Ala-Arg-Ser-Lys-Lys-NH$_2$, the following Boc-amino acids were used in sequence: Boc-Lys(Cl-Z); Boc-Lys(Cl-Z); Boc-Ser(Bzl); Aoc-Arg(Tos); Boc-Ala; Boc-Pro; Boc-Thr(Bzl); Boc-Pro; Boc-Tyr(Bzl); Boc-Ala; Aoc-Arg(Tos); Boc-D-Ser(Bzl). In all steps calling for addition of a Boc- or Aoc-AA, the AA is added at 2.5 meq per g resin.

EXAMPLE II

The inhibitory activity of the compounds synthesized on LH-induced ovulation was tested in female rats. Virgin female Sprague-Dawley rats, weighing from 230–280 g and having two consecutive 4 day vaginal cycles, were housed in an air-conditioned room with the lights on from 5:00 a.m. to 7:00 p.m. On the early afternoon of proestrus, the rats were injected with at least 31.5 mg/kg of Nembutal to render them unconscious. The unconscious state blocks the rats' endogenous release of LH. Between 1:30 and 2:00 p.m., 10 $\mu$g lutropin, NIH-LH S$_{17}$, obtainable from the National Institute of Health, or 5 $\mu$g human choriogonadotropin, hCG CR 117, also obtainable from the National Institute of Health, was injected into the jugular vein. One minute later, one of the inventive synthesized polypeptides chosen from the group consisting of D-Ser-Arg-Ala-Tyr-Pro-Thr-Pro-Ala-Arg-Ser-Lys-Lys-NH$_2$, D-Ser-Arg-Tyr-Gly-Lys-Pro-Val-Gly-Lys-Lys-Lys-Lys-NH$_2$, D-Ser-Pro-Val-Gly-Val-NH$_2$ and D-Ser-Arg-Tyr-Gly-Pro-Val-Gly-Val-NH$_2$ was injected in saline solution into the rat. Additional synthesized peptides were injected at 20 minutes and 40 minutes thereafter.

Control rats receiving only Nembutal did not ovulate. However, all rats receiving LH or hCG following the Nembutal ovulated 8 to 12 eggs. Between 10:00 and 11:00 A.M. the following morning, the rats were dissected and the eggs in the fallopian tubes were counted by the use of a low-power microscope.

The minimum effective dose was not established, but for example, Compound E$_2$ injected at 50 to 200 $\mu$g per rat, 1 minute, 20 minutes and 40 minutes after LH, completely blocked ovulation. The inventor's other compounds were less effective. An example of testing results is summarized in Table I. The compound abbreviations are as follows:

E$_2$ D-Ser-Arg-Tyr-Gly-Pro-Val-Gly-Val-NH$_2$
I  D-Ser-Arg-Ala-Tyr-Pro-Thr-Pro-Ala-Arg-Ser-Lys-Lys-NH$_2$
III D-Ser-Arg-Tyr-Gly-Lys-Pro-Val-Gly-Lys-Lys-Lys-Lys-NH$_2$
E$_1$ D-Ser-Pro-Val-Gly-Val-NH$_2$

TABLE I

Effect of Inhibitor Compounds on Lutropin Induced Ovulation in the Nembutal-Blocked Rat

| Compound | Dose | Number of Animals | | Average number of Eggs | |
|---|---|---|---|---|---|
| | | LH | LH + Compound | LH | LH + Compound |
| E$_2$ | 200$\mu$g | 6 | 8 | 10 | 0 |
| E$_2$ | 100$\mu$g | 3 | 8 | 11 | 0 |

TABLE I-continued
Effect of Inhibitor Compounds on Lutropin Induced Ovulation in the Nembutal-Blocked Rat

| Compound | Dose | Number of Animals LH | Number of Animals LH + Compound | Average number of Eggs LH | Average number of Eggs LH + Compound |
|---|---|---|---|---|---|
| $E_2$ | 50μg | 1 | 2 | 10 | 0 |
| I | 100μg | 4 | 4 | 11 | 8 |
| I | 50μg | 2 | 2 | 10 | 6 |
| I | 20μg | 2 | 3 | 12 | 10 |
| III | 300μg | 1 | 3 | 12 | 5 |
| III | 200μg | 1 | 3 | 12 | 10 |
| III | 100μg | 1 | 3 | 12 | 10 |
| $E_1$ | 100μg | 3 | 2 | 12 | 8 |

EXAMPLE III

An in vitro experiment was performed to determine the effect of the inventor's compounds on Lutropin stimulation of RNA synthesis in Corpora Lutea Chromatin. $E_2$ and other inventive compounds inhibit lutropin stimulation of RNA synthesis by DNA-dependent RNA polymerases associated with chromatin prepared from the nuclei of the corpus luteum of the ovary. The chromatin containing the DNA-Dependent RNA polymerases was prepared from purified nuclei isolated from bovine corpus luteum by means well known in the art. The methods and materials used for assessing RNA synthesis in vitro are described in detail in McKerns and Ryschkewitsch, 478 Biochim. Biophys. Acta 68 (1977).

In these experiments, the effect of Lutropin, $E_1$, a combination of Lutropin and $E_1$, $E_2$, a combination of Lutropin and $E_2$, Compound IV, and a combination of Lutropin and Compound IV on RNA Synthesis is compared to a control. Radioactive [8-$^{14}$C] adenosine triphosphate was used in each mixture to monitor the effect on RNA synthesis. In each specific instance, a high-ionic strength incubation buffer such as described in the McKerns publication and which favors polymerase II was used. Polymerase II is a compound which synthesizes mRNA. Incubation lasted for about 5 minutes at a temperature of approximately 25° C.

During incubation, the radioactive adenosine triphosphate was incorporated into the RNA of the chromatin in vitro. After incubation, the RNA was isolated from the chromatin and the amount of radioactivity measured in a liquid scintillation spectrometer.

The values given in Table II represent the mean of three closely agreeing values. Lutropin and the inventive compounds were at a final concentration of $10^{-9}$ M. As is seen from the results, in one control, 230 pico moles (pmol) of the radioactive labeled ATP was incorporated into RNA. Addition of lutropin greatly increased this incorporation to 1290 pmol. However, the incorporation in the presence of lutropin and compound $E_2$ was reduced back to a value closely corresponding to the control level. As is evident from the results the other inventive compounds were less effective than $E_2$.

TABLE II
Effect of Inhibitor Compounds on Lutropin Stimulation of RNA Synthesis in Corpora Lutea Chromatin

| | pmol[8-$^{14}$C]ATP Incorporated |
|---|---|
| Control | 230 |
| Lutropin | 1290 |
| $E_1$ | 420 |
| Lutropin + $E_1$ | 1190 |
| $E_2$ | 220 |
| Lutropin + $E_2$ | 260 |
| Control | 1790 |
| Lutropin | 3100 |
| Compound IV | 2070 |
| Lutropin + Comp. IV | 2400 |

Compounds $E_1$ and $E_2$ are the same as in Example II. Compound IV is D-Ser-Arg-Tyr-Gly-Lys-Pro-Val-Arg-Ser-Lys-Lys-NH$_2$.

What is claimed is:

1. A compound $R_1$-$R_2$-$R_3$ and its pharmacologically acceptable salts, wherein $R_1$ is chosen from the group consisting of D-Ser-Arg, Ser-Arg, and -Arg, $R_2$ is chosen from the group consisting of Tyr-Gly-Lys-Pro-Val-Gly-Lys-Lys, Ala-Tyr-Pro-Thr-Pro-Ala-Arg-Ser-Lys, Tyr-Gly-Lys-Pro-Val-Gly-Lys-Lys-Lys, Tyr-Gly-Lys-Pro-Val-Arg-Ser-Lys, Tyr-Gly-Pro, Tyr-Gly-Pro-Val-Gly, Val-Leu-Pro, Val-Leu-Val-Gly, Ala-Tyr-Pro, Leu-Pro-Gly-Pro, Val-Leu-Gln-Gly, Ala-Tyr-Pro-Arg-Leu-Pro-Gly, Ala-Tyr-Pro-Arg-Val-Leu-Gln-Gly and Ala-Tyr-Pro-Arg-Val-Leu-Pro, and $R_3$ is chosen from the group consisting of Val-NH$_2$, -Val, Lys-NH$_2$, -Lys, -Thr, Thr-NH$_2$, -Ser, Ser-NH$_2$, -Pro and -Pro-NH$_2$.

2. A compound of claim 1 comprising $R_1$-Tyr-Gly-$R_6$ and its pharmacologically acceptable salts, wherein $R_6$ is chosen from the group consisting of Pro-$R_4$ and Pro-Val-Gly-$R_4$ wherein $R_4$ is chosen from the group consisting of -Val-NH$_2$ and -Val.

3. A compound of claim 2 wherein Tyr may be substituted by an amino acid chosen from the group consisting of Ala, Val, and Leu, Gly may be substituted by an amino acid chosen from the group consisting of Tyr, Leu, and Pro and Val-NH$_2$ may be substituted by a compound chosen from the group consisting of Pro-NH$_2$, Gly, Thr and Thr-NH$_2$.

4. A compound of claim 3 comprising D-Ser-Arg-Val-Leu-Pro-Val-NH$_2$ and its pharmacologically acceptable salts.

5. A compound of claim 3 comprising D-Ser-Arg-Ala-Tyr-Pro-Thr and its pharmacologically acceptable salts.

6. A compound of claim 3 comprising D-Ser-Arg-Ala-Tyr-Pro-Thr-NH$_2$ and its pharmacologically acceptable salts.

7. A compound of claim 2 comprising D-Ser-Arg-Tyr-Gly-Pro-Val-Gly-Val-NH$_2$ and its pharmacologically acceptable salts.

8. A compound of claim 2 comprising D-Ser-Arg-Tyr-Gly-Pro-Val-NH$_2$ and its pharmacologically acceptable salts.

9. A compound of claim 1 comprising $R_1$-Tyr-Gly-Lys-Pro-Val-Gly-Lys-Lys-$R_4$, and its pharmacologically acceptable salts wherein $R_4$ is chosen from the group consisting of -Val-NH$_2$ and -Val.

10. A compound of claim 9 comprising D-Ser-Arg-Tyr-Gly-Lys-Pro-Val-Gly-Lys-Lys-Val-NH$_2$ and its pharmacologically acceptable salts.

11. A compound of claim 1 comprising $R_1$-Ala-Tyr-Pro-Thr-Pro-Ala-Arg-Ser-Lys-$R_5$, and its pharmacologically acceptable salts wherein $R_5$ is chosen from the group consisting of -Lys-NH$_2$ and -Lys.

12. A compound of claim 11 comprising D-Ser-Arg-Ala-Tyr-Pro-Thr-Pro-Ala-Arg-Ser-Lys-Lys-NH$_2$ and its pharmacologically acceptable salts.

13. A compound of claim 1 comprising $R_1$-Tyr-Gly-Lys-Pro-Val-Gly-Lys-Lys-Lys-$R_5$ and its pharmacologically acceptable salts wherein $R_5$ is chosen from the group consisting of -Lys-NH$_2$ and -Lys.

14. A compound of claim 13 comprising D-Ser-Arg-Tyr-Gly-Lys-Pro-Val-Gly-Lys-Lys-Lys-NH$_2$ and its pharmacologically acceptable salts.

15. A compound of claim 1 comprising $R_1$-Tyr-Gly-Lys-Pro-Val-Arg-Ser-Lys-$R_5$, and its pharmacologically acceptable salts wherein $R_5$ is chosen from the group consisting of -Lys-NH$_2$ and -Lys.

16. A compound of claim 15 comprising D-Ser-Arg-Tyr-Gly-Lys-Pro-Val-Arg-Ser-Lys-Lys-NH$_2$ and its pharmacologically acceptable salts.

17. A compound of claim 1 comprising $R_1$-Val-Leu-Val-Gly-$R_4$, and its pharmacologically acceptable salts, wherein $R_4$ is chosen from the group consisting of Val-NH$_2$ and -Val.

18. A compound of claim 17 comprising D-Ser-Arg-Val-Leu-Val-Gly-Val-NH$_2$, and its pharmacologically acceptable salts.

19. A compound of claim 1 comprising $R_1$-Leu-Pro-Gly-Pro-$R_7$, and its pharmacologically acceptable salts, wherein $R_7$ is chosen from the group consisting of Ser-NH$_2$ and Ser.

20. A compound of claim 19 comprising D-Ser-Arg-Leu-Pro-Gly-Pro-Ser-NH$_2$ and its pharmacologically acceptable salts.

21. A compound of claim 1 comprising $R_1$-Val-Leu-Gln-Gly-$R_4$ and its pharmacologically acceptable salts, wherein $R_4$ is chosen from the group consisting of Val-NH$_2$ and -Val.

22. A compound of claim 21 comprising D-Ser-Arg-Val-Leu-Gln-Gly-Val-NH$_2$ and its pharmacologically acceptable salts.

23. A compound of claim 1 comprising $R_1$-Ala-Tyr-Pro-Arg-Leu-Pro-Gly-$R_8$, and its pharmacologically acceptable salts, wherein $R_8$ is chosen from the group consisting of Pro-NH$_2$ and -Pro.

24. A compound of claim 23 comprising D-Ser-Arg-Ala-Tyr-Pro-Arg-Leu-Pro-Gly-Pro-NH$_2$ and its pharmacologically acceptable salts.

25. A compound of claim 1 comprising $R_1$-Ala-Tyr-Pro-Arg-Val-Leu-Gln-Gly-$R_4$ and its pharmacologically acceptable salts wherein $R_4$ is chosen from the group consisting of Val-NH$_2$ and -Val.

26. A compound of claim 25 comprising D-Ser-Arg-Ala-Tyr-Pro-Arg-Val-Leu-Gln-Gly-Val-NH$_2$ and its pharmacologically acceptable salts.

27. A compound of claim 1 comprising $R_1$-Ala-Tyr-Pro-Arg-Val-Leu-Pro-$R_4$, and its pharmacologically acceptable salts wherein $R_4$ is chosen from the group consisting of Val-NH$_2$ and -Val.

28. A compound of claim 27 comprising D-Ser-Arg-Ala-Tyr-Pro-Arg-Val-Leu-Pro-Val-NH$_2$ and its pharmacologically acceptable salts.

* * * * *